(12) United States Patent
Dehmer

(10) Patent No.: US 9,803,782 B2
(45) Date of Patent: Oct. 31, 2017

(54) FITTING ELEMENT WITH HYDRAULIC GRIP FORCE ELEMENT

(75) Inventor: Bernhard Dehmer, Rastatt (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1156 days.

(21) Appl. No.: 13/695,878

(22) PCT Filed: May 3, 2010

(86) PCT No.: PCT/EP2010/055971
§ 371 (c)(1),
(2), (4) Date: Dec. 4, 2012

(87) PCT Pub. No.: WO2011/137924
PCT Pub. Date: Nov. 10, 2011

(65) Prior Publication Data
US 2013/0134082 A1    May 30, 2013

(51) Int. Cl.
| | | |
|---|---|---|
| *F16L 17/10* | (2006.01) | |
| *F16L 19/04* | (2006.01) | |
| *F16L 19/06* | (2006.01) | |
| *G01N 30/60* | (2006.01) | |
| *B01D 15/14* | (2006.01) | |
| *F16L 19/07* | (2006.01) | |

(52) U.S. Cl.
CPC .............. *F16L 17/10* (2013.01); *B01D 15/14* (2013.01); *F16L 19/041* (2013.01); *F16L 19/046* (2013.01); *F16L 19/06* (2013.01); *F16L 19/07* (2013.01); *G01N 30/6039* (2013.01)

(58) Field of Classification Search
CPC ......... F16L 17/10; F16L 19/046; F16L 19/06; G01N 30/6039
USPC ..... 285/100, 101, 102, 103, 109, 348, 382.7
See application file for complete search history.

(56) References Cited

U.S. PATENT DOCUMENTS

| | | | | |
|---|---|---|---|---|
| 3,713,204 A | * | 1/1973 | Arnold ................. | F16L 21/007 285/101 |
| 3,713,675 A | * | 1/1973 | White, Jr. ............ | F16L 37/002 285/18 |
| 3,784,234 A | * | 1/1974 | Mohr .................... | F16L 37/002 285/104 |
| 3,810,665 A | | 5/1974 | Rodgers | |
| 3,843,167 A | * | 10/1974 | Gronstedt .............. | F16L 17/10 174/84 R |
| 4,059,288 A | * | 11/1977 | Mohr .................... | F16L 37/002 285/101 |

(Continued)

FOREIGN PATENT DOCUMENTS

| | | |
|---|---|---|
| CN | 1902425 A | 1/2007 |
| EP | 309596 | 9/1987 |

(Continued)

*Primary Examiner* — James M Hewitt

(57) ABSTRACT

A fitting element, in particular for an HPLC application, is configured for providing a fluidic coupling of a tubing to a fluidic device. The fitting element comprises a gripping piece to exert—upon coupling of the tubing to the fluidic device—a grip force (G) between the fitting element and the tubing. The gripping piece comprises a hydraulic element configured to transform an axial force (S) into a hydraulic pressure (P) within the hydraulic element. The hydraulic pressure (P) in the hydraulic element causes the grip force (G).

21 Claims, 3 Drawing Sheets

(56) References Cited

U.S. PATENT DOCUMENTS

| | | | |
|---|---|---|---|
| 4,178,020 A * | 12/1979 | Dopyera | F16L 37/002 |
| | | | 277/607 |
| 4,982,597 A | 1/1991 | Berger | |
| 5,074,599 A | 12/1991 | Wirbel et al. | |
| 5,286,066 A * | 2/1994 | Yang | F16L 17/10 |
| | | | 285/105 |
| 5,826,887 A * | 10/1998 | Neumann | F16J 15/46 |
| | | | 277/605 |
| 6,494,500 B1 | 12/2002 | Todosiev et al. | |
| 8,439,404 B2 * | 5/2013 | Anton | F16J 15/064 |
| | | | 285/382.7 |
| 2006/0113794 A1 | 6/2006 | Plant et al. | |
| 2008/0237112 A1 | 10/2008 | Ford et al. | |
| 2011/0303593 A1 * | 12/2011 | Reinhardt | F16L 19/061 |
| | | | 210/143 |

FOREIGN PATENT DOCUMENTS

| | | |
|---|---|---|
| EP | 1577012 B1 | 11/2014 |
| GB | 1170921 | 11/1969 |
| GB | 2451628 A | 11/2009 |
| WO | 2005084337 A2 | 9/2005 |
| WO | 2009088663 A1 | 7/2009 |
| WO | 2010/000324 A1 | 1/2010 |
| WO | 2010/045963 A1 | 4/2010 |
| WO | 2011/076244 A1 | 6/2011 |

\* cited by examiner

FITTING ELEMENT WITH HYDRAULIC GRIP FORCE ELEMENT

BACKGROUND ART

The present invention relates to a fitting element for a fluidic device, in particular in a high performance liquid chromatography application.

The present application is the national stage of International Patent Application No. PCT/EP2010/055971, filed May 3, 2010, the entire contents of which are incorporated herein by reference.

In high performance liquid chromatography (HPLC), a liquid has to be provided usually at a very controlled flow rate (e.g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid which may then be identified.

The mobile phase, for example a solvent, is pumped under high pressure typically through a column of packing medium (also referred to as packing material), and the sample (e.g. a chemical or biological mixture) to be analyzed is injected into the column. As the sample passes through the column with the liquid, the different compounds, each one having a different affinity for the packing medium, move through the column at different speeds. Those compounds having greater affinity for the packing medium move more slowly through the column than those having less affinity, and this speed differential results in the compounds being separated from one another as they pass through the column.

The mobile phase with the separated compounds exits the column and passes through a detector, which identifies the molecules, for example by spectrophotometric absorbance measurements. A two-dimensional plot of the detector measurements against elution time or volume, known as a chromatogram, may be made, and from the chromatogram the compounds may be identified. For each compound, the chromatogram displays a separate curve or "peak". Effective separation of the compounds by the column is advantageous because it provides for measurements yielding well defined peaks having sharp maxima inflection points and narrow base widths, allowing excellent resolution and reliable identification of the mixture constituents. Broad peaks, caused by poor column performance, so called "Internal Band Broadening" or poor system performance, so called "External Band Broadening" are undesirable as they may allow minor components of the mixture to be masked by major components and go unidentified.

An HPLC column typically comprises a stainless steel tube having a bore containing a packing medium comprising, for example, silane derivatized silica spheres having a diameter between 0.5 to 50 µm, or 1-10 µm or even 1-7 µm. The medium is packed under pressure in highly uniform layers which ensure a uniform flow of the transport liquid and the sample through the column to promote effective separation of the sample constituents. The packing medium is contained within the bore by porous plugs, known as "frits", positioned at opposite ends of the tube. The porous frits allow the transport liquid and the chemical sample to pass while retaining the packing medium within the bore. After being filled, the column may be coupled or connected to other elements (like a control unit, a pump, containers including samples to be analyzed) by e.g. using fitting elements. Such fitting elements may contain porous parts such as screens or frit elements.

During operation, a flow of the mobile phase traverses the column filled with the stationary phase, and due to the physical interaction between the mobile phase and the stationary phase a separation of different compounds or components may be achieved. In case the mobile phase contains the sample fluid, the separation characteristics are usually adapted in order to separate compounds of such sample fluid. The term compound, as used herein, shall cover compounds which might comprise one or more different components. The stationary phase is subject to a mechanical force generated in particular by a hydraulic pump that pumps the mobile phase usually from an upstream connection of the column to a downstream connection of the column. As a result of flow, depending on the physical properties of the stationary phase and the mobile phase, a relatively high pressure occurs across the column.

Fittings for coupling different components, such as separation columns and conduits, of fluidic devices are commercially available and are offered, for instance, by the company Swagelok (see for instance the website swagelok.com). A typical tube fitting is disclosed in U.S. Pat. No. 5,074,599 A.

U.S. Pat. No. 6,494,500 discloses a self-adjusting high pressure liquid connector for use with high pressure liquid chromatography (HPLC) columns requiring liquid-tight and leak free seals between fittings and unions.

WO 2005/084337 discloses a coupling element comprising a male sealing element. The male sealing element may have a generally cylindrical shape, and defines a fluid passageway therethrough for the transmission of fluid. The male sealing element is secured to a ferrule which is located within a cavity of the nut. The coupling element also has a biasing element disposed between a retaining ring and the ferrule located within the nut cavity. This biasing element facilitates a fluid-tight, metal to metal (or metal to plastic, or plastic to plastic) seal between the male sealing element and female sealing element.

WO 2009/088663 A1 discloses liquid-chromatography conduit assemblies having high-pressure seals. A fluid-tight seal, proximal to the joint between two conduits, is provided, for example, through use of pressure, while a stabilizing seal, distal to the joint, is provided by adhering the conduits to the tube.

A high pressure connect fitting is disclosed at US 2008/0237112 A1. A tip of a seal contacts the walls of a tapered sealing cavity to form a primary seal. The volume of space between the very end of the tip and the end of a sealing cavity defines a dead space. As the seal is axially compressed within an annular recess, the tip engages the walls of the tapered sealing cavity to form the primary seal, and further deforms to occupy space otherwise associated with the dead space. As the tip of the seal engages the tapered sealing cavity, the end face of the seal compresses against the end of the annular recess to form a secondary seal extending radially around the tip of the seal.

WO 2010/000324 A1, by the same inventor, discloses a fitting for coupling a tubing to another component of a fluidic device. The fitting comprises a male piece having a front ferrule and a back ferrule both being slidable on the tubing. The male piece has a first joint element configured slidably on the tubing. A female piece has a recess configured for accommodating the front ferrule and the tubing, and a second joint element configured to be joinable to the first joint element. The back ferrule is configured in such a manner that, upon joining the first joint element to the second joint element, the back ferrule exerts a pressing force on the front ferrule to provide a sealing between the front ferrule and the female piece, and the back ferrule exerts a grip force between the male piece and the tubing.

DISCLOSURE

It is an object of the invention to provide an improved fitting, in particular for HPLC applications.

According to embodiments of the present invention, a fitting element is provided, in particular for an HPLC application. The fitting element is configured for providing a fluidic coupling of a tubing to a fluidic device. The fitting element comprises a gripping piece configured to exert a grip force between the fitting element and the tubing, when the tubing is coupled to the fluidic device. The gripping piece comprises a hydraulic element configured to transform an axial force into a hydraulic pressure within the hydraulic element. The hydraulic pressure in the hydraulic element then causes the grip force.

The gripping piece promotes the grip force to mechanically connect the gripping element with the tubing, when the tubing is coupled to the fluidic device.

In the mechanical solutions as known in the art, the grip force results from changing an initial force in its direction by use of mechanical devices in accordance with the parallelogram rule of vector addition, as, for example, described in the aforementioned WO2010/000324A1. In contrast thereto, the invention provides an entirely different path by first transforming a force into a hydraulic pressure, which then exerts the grip force resulting from abutting of the hydraulic element to another device, such as the tubing or a device in-between. Designing the abutting surface allows to design the magnitude as well as the force distribution along such abutting surface(s). Dependent on the material used for the hydraulic element, pressure within the hydraulic element will be substantially equal (at least after a certain relaxation time), so that the hydraulic element can provide substantially the same grip force along the abutting surface(s). This can be of great advantage over mechanical solutions (with mechanical force redirection), as such mechanical solutions typically provide a high contact pressure on a small contact surface.

In embodiments, the hydraulic element is one of an isotropic hydraulic element and an anisotropic hydraulic element. An isotropic hydraulic element can be understood as such hydraulic element which transforms an applied force into an isotropic pressure within the hydraulic element—at least after a given time period or at a given time constant. In such isotropic hydraulic element, pressure at a boundary surface of the hydraulic element is substantially equal, so that substantially the same force is exerted on a standardized surface element (i.e. a surface element standardized to a given area) of the boundary surface. Isotropic hydraulic elements may typically comprise a liquid.

An anisotropic hydraulic element can be understood as such hydraulic element which transforms an applied force into a pressure distribution within the hydraulic element—at least after a given time period or at a given time constant. The pressure distribution may result from superimposition of both an isotropic pressure behavior and an internal stress of the anisotropic hydraulic element. The anisotropic hydraulic element is preferably configured so that the isotropic pressure behavior dominates over the internal stress. In anisotropic hydraulic elements, pressure at the boundary surface of the hydraulic element varies in accordance with the pressure distribution, so that force exerted on a respective standardized surface element (i.e. a surface element standardized to a given area) at the boundary surface also varies in accordance with the pressure distribution. Anisotropic hydraulic elements typically comprise a solid (phase) material having a high elasticity, such as an elastomer.

In embodiments, the material of the isotropic hydraulic element is configured to transform an applied force into an isotropic pressure within the hydraulic element, so that the pressure within the hydraulic element is independent on the direction of the applied force. Using embodiments of the anisotropic hydraulic element may allow adding to the viscosity or plasticity of the hydraulic element an elastic or memory behavior to increase anisotropic behavior, so that the force can be distributed as desired. This may be used e.g. to design for better releasing behavior when unlocked.

Embodiments of the isotropic hydraulic element may be configured to provide high plasticity and deformability in order to distribute a substantially isotropic pressure. The requirements with respect to viscosity may vary from application to application and result, on one hand, from a requirement that the pressure within the hydraulic element is substantially equal (at least after a given time), which might require a lower viscosity. On the other hand, viscosity might not be too low in order to avoid or reduce potential leakage in particular towards moveable components and/or a sealing gap. Accordingly, the viscosity may be selected to best fit such contravening requirements.

The hydraulic element may be or comprise a fluid, a gel, a plastic material, and or any other suitable material allowing generating such hydraulic pressure within the hydraulic element. The fluid may be a liquid, an oil such as a pressure oil, grease, or any other suitable fluid. The gel might be e.g. of polysiloxane, a silicone gel such as WACKER SilGe. The plastic material can be a polymer such as a polymer having high plasticity, in particular rubber, polyurethane, polytetrafluoroethylene (PTFE, e.g. TEFLON® material), or any other suitable plastic material.

The material of the hydraulic element can be configured to be self sealing (e.g. with respect to any clearing surrounding or coupling to the hydraulic element) but may also be provided sealed within an enveloping housing.

The gripping piece might comprise a housing or shell for housing the hydraulic element. Such housing might be in particular useful for retaining the hydraulic element in a certain space and also to avoid that the hydraulic element might creep away or leak from such space. The housing might be provided by an integral housing or by different elements abutting at each other and thus providing the space for containing the hydraulic element.

Embodiments of the hydraulic element may have an absolute or so called dynamic viscosity in the range of 250-100000 mPa*s, and preferably in the range of 1000 to 25000 mPa*s.

Embodiments of the hydraulic element may also be specified in hardness Shore A in a range of 10 to 100 and Shore D in a range 30 to 100 and preferably in the range 70 Shore A to 80 Shore D. In an example, a polyurethane elastomer having a hardness of 90 Shore A has been found suitable. Higher viscosity or hardness of the hydraulic element in combination with the memory effect on the original shape helps to relax the gripping force when unlocked.

Embodiments of hydraulic elements (in particular such not comprising a liquid) may have an elasticity measured in elongation before break in a range of 10% to 1000%, where 30% or higher might be feasible for many designs.

The hydraulic element can have an active contact surface directed towards the tubing. The active contact surface transforms the hydraulic pressure into the grip force. The size of the contact surface can be configured to adjust to a desired magnitude and/or profile of force distribution of the grip force. The hydraulic element may have a plane (or planar) surface abutting to the tubing, so that the plane surface substantially represents the active contact surface. The active contact surface may exert a substantially homogeneous profile of the grip force along the axial direction.

By adequately designing the contact surface by which the hydraulic element is abutting to the tubing or an element in-between, the force acting on the tubing can be configured. For example, in case the pressure within the hydraulic element is maintained constant, the exerted force on the tubing can be increased by increasing the contact surface or decreased by decreasing the contact surface. This results from the hydraulic element having a substantially homogeneous and equal exertion of the gripping force all along the contact surface (e.g. towards the tubing). Accordingly, the same total holding force as in mechanical prior art solutions can be achieved by embodiments of the present invention having a smaller (maximum) contact pressure, which in turn may reduce or even avoid damaging of the tubing. On the other hand, by increasing the contact surface, for example by prolonging the hydraulic element in axial direction, the gripping force exerting in total can be almost arbitrarily increased as long as the hydraulic pressure is maintained. For a given total gripping force, the hydraulic pressure can be reduced by increasing the contact surface.

In one embodiment, the gripping piece is configured for generating a spring-biased force upon coupling of the tubing to the fluidic device. The term "spring-biased force" can be understood as a force, which is still exerted on an object in similar size even when the object is displaced—within certain limitations. The spring-biased force may also be an elastic and/or a spring-loaded force.

The spring-biased force can be exerted in an axial and/or radial direction. Axial direction shall mean a direction of an axial elongation of the tubing or parallel thereto. Radial shall mean a direction perpendicular to the axial elongation of the tubing or parallel thereto. Radial can also mean the radial elongation of the tubing.

The gripping piece can be configured for exerting the spring-biased force in radial direction of the tubing in order to provide a spring-biased grip force onto the tubing. This can be of advantage in order to compensate for mechanical tolerances, creeping of elements involved, and/or dynamic behavior of the system. In particular dynamic effects of the mobile phase may thus be compensated. Alternatively or in addition, the gripping piece may be configured for exerting the spring-biased force in axial direction on the tubing in order to provide a spring-biased coupling of the tubing to the fluidic device. In particular, a spring biased-pressing force on a front-side of the tubing can thus be achieved. This can promote a forward motion of the tubing towards the fluidic device. The spring-biased force in axial direction on the tubing may also allow compensating for mechanical tolerances or dynamic behavior, in particular caused by pressure variations in the fluid conducted by the tubing. In HPLC, such pressure variations often result from switching a sample loop into the flow path between the pump and the column.

Alternatively or in addition, the gripping piece can be configured for exerting the spring-biased force in axial direction on a sealing piece in order to provide a spring-biased sealing between the sealing piece and the fluidic device. The sealing piece can provide a fluid tight sealing in order to seal the fluid under high pressure in the tubing against ambient (i.e. outside the tubing). Again, the spring-bias may allow compensating mechanical tolerances and/or dynamic behavior of components involved. The spring-biased force can be generated by a mechanical spring element such as a spring washer, a disc spring. A multi spring configuration might be used, for example to disc spring separated by a flat spring. Alternatively or in addition, an elastic shaping can be provided to generate the spring biased force. For example, the gripping piece and/or the hydraulic element (in particular a housing thereof) can be shaped adequately to generate the spring biased force.

The spring biased force may also or in addition be generated by the hydraulic element. For that purpose, the hydraulic element may for example comprise one or more gas inclusions, which can be compressed under the influence of pressure but which will elastically counteract on reduction or removal of the applied pressure. Alternatively or in addition, the material of the hydraulic element may be selected to have an elastic compressibility within a range of 5% to 30% at nominal hydraulic pressure. Alternatively or in addition, a housing of the hydraulic element may be provided to be at least partly elastic in order to provide the elastic, spring-biased force.

In one embodiment, the fitting element comprises a sealing piece configured to provide a sealing between the sealing piece and the fluidic device, when the tubing is coupled to the fluidic device. The sealing piece may be or comprise a front ferrule, for example as disclosed in the introductory part of the description such as by the aforementioned WO 2010/000324 A1, which teaching with respect to the sealing piece shall be incorporated herein by reference. The gripping piece may exert a pressing force against the sealing piece, which may be at least partially caused by the hydraulic pressure of the hydraulic element. The pressing force may be spring-biased in particular to address dynamic behavior of the system. The sealing piece can be provided slidable on the tubing, at least before coupling of the tubing to the fluidic device. This can allow to easily move the sealing piece into its intended position for sealing.

The sealing piece may have a conically tapered front part configured to correspond to a conical portion of a receiving cavity of the fluidic device. Upon coupling of the tubing to the fluidic device, the conically tapered front part may press against the conical portion of the receiving cavity for sealing against a pressure in a fluid part of the tubing.

In one embodiment, the fitting element comprises a front sealing configured to provide a sealing between a front side of the tubing and the fluidic device, when the tubing couples to the fluidic device. Such front sealing may in particular be a sealing in addition to the sealing provided by the sealing piece, but may also be an alternative thereto. In a preferred embodiment, the front sealing can be provided by an inlay comprised in a cavity of the front side of the tubing, such as disclosed in International Application No. PCT/EP2009/067646, which teaching with respect to the inlay shall be incorporated herein by reference.

In one embodiment, wherein the fitting element comprises the sealing piece (configured for sealing against a pressure in the fluid part of the tubing) and a front sealing, the fitting element provides a two-stage sealing with the front sealing sealing directly where the tubing couples to the fluidic device, and the sealing piece providing an additional sealing stage in order to securely sealing against a fluid pressure in the fluid path. In other words, the front sealing may provide a low(er) pressure sealing at the front side of the tubing, and the sealing piece may provide a high(er) pressure sealing located, for example, at or along a lateral side of the tubing.

It is to be understood that the front side at the connection of the tubing to the fluidic device is often very difficult to seal, as in particular the shape of the counterpart element to the tubing might vary from one fluidic device to another and/or might have surface imperfections. However, contact pressure in particular in axial direction of the tubing might be limited in order to avoid or reduce destruction or deformation of the components involved. With increasing fluid pressure, for example in the range of thousand bar and beyond, conventional fitting systems have been often shown not to be sufficient and may lead to leaking and/or cross contamination. The two-stage sealing, however, may allow that fluid even when "leaking" through the first stage of the front sealing is fully sealed at the second stage and is limited from returning back into the fluid path, for example during normal application.

For example in an HPLC application, the front sealing may allow fluid to pass ("leak") during pressurizing of the system (when the pressure in the system is raised to the desired target pressure). While the sealing piece fully seals so that no fluid can leak through such sealing piece, an interspace between the first and second sealing stages may become filled with fluid. However, as such fluid applied in the pressurizing phase in HPLC is normally only solvent which does not contain any sample, the interspace between the first and second stages will thus be filled only with such (non sample containing) solvent, so that no sample contamination can occur even when fluid contained in the inner space may return back into the fluid path. Further, it is to be understood that system pressure after sample is introduced in HPLC usually changes slowly and within a narrow range compared to the system pressure. so that the fluid in the interspace, is kept within the interspace and "sees" only very low "driving force" to communicate with the fluidic path of the inside of the tubing. Such embodiments thus provide a "chromatographic sealing" at the front side by means of the front sealing and a "system pressure sealing" by means of the sealing piece. The term "chromatographic sealing" can be understood as a sealing sufficient during a sample run in an HPLC system, so that carry over (i.e. the sample is temporally trapped and released later), or external band broadening (e.g. sample is guided to a "dead space" where the sample is released only by diffusion) can be avoided or at least limited, preferably while maintaining pressure within a narrow range when sample has been introduced in the HPLC-System.

In one embodiment, the fitting element comprises a first joint element configured for exerting the axial force on the hydraulic element, when the tubing is coupled to the fluidic device. The first joint element can be joined to a second joint element of the fluidic device, for example by a screw connection. The first joint element may be provided slidable on the tubing, at least before coupling of the tubing to fluidic device, so that the first joint element can be easily moved into its desired position. The first joint element may partly house the hydraulic element, for example by providing at least one side enclosing the hydraulic element.

The axial force, as exerting on the hydraulic element, can be converted in a radial direction perpendicular to an axial elongation of the tubing. The axial force may result from coupling of the tubing to the fluidic device, for example from joining the joint elements together.

The fitting element can be configured to become accommodated by a receiving cavity of the fluidic device, for example in accordance with embodiments as disclosed by the documents cited in the introductory part of the description, which teaching with respect to accommodating the fitting element shall be incorporated herein by reference.

The gripping force can be in a radial direction with respect to the tubing.

In embodiments, the gripping piece is or comprises a back ferrule and/or may be slidable on the tubing at least before coupling of the tubing to the fluidic device, so that the gripping piece can easily be moved into its desired position. This can be in accordance with embodiments as disclosed by documents cited in the introductory part of the description, which teaching with respect to such mechanical aspects of the gripping piece (e.g. back ferrule or slidability) shall be incorporated herein by reference.

In embodiments, the tubing is made of or comprises a metal, stainless steel, titan, plastic, polymer, ceramic, glass and/or quartz. The tubing may have a lumen having a diameter of less than 0.8 mm, particularly less than 0.2 mm. The tubing may have circular, elliptical, rectangular or any other suitable shape as known in the art and may also show variations in diameter and/or shaping. The tubing may be or comprise a capillary.

In one embodiment, the tubing comprises an inner tubing and an outer tubing. The outer tubing (radially) surrounds the inner tubing. The inner tubing may be comprised of a material different from the outer tubing. The outer tubing may be a socket for adapting to a desired outer diameter for the tubing and/or specific requirements for further tightening elements e.g. ferrules.

The terms "fitting" and "fitting element", as used herein, shall both relate to coupling a tubing to a fluidic device. The term "fitting" shall cover all components required for coupling the tubing to the fluidic device, and may even comprise the tubing and/or the fluidic device, or parts thereof. The term "fitting element" shall cover a part of the fitting.

In an embodiment of the fitting, the fitting element comprises a front ferrule, a back ferrule, and a first joint element. The receiving cavity of the fluidic device is configured for accommodating the front ferrule and the tubing and has a second joint element configured to be joinable to the first joint element of the fitting element. The back ferrule is configured in such a manner that—upon joining the first joint element to the second joint element—the back ferrule exerts a spring-biased pressing force against the front ferrule to provide a sealing between the front ferrule and the receiving cavity. Further upon joining the first and second joined elements, the back ferrule exerts a grip force on the tubing.

In such embodiment, the front ferrule, the back ferrule, and the first joint element may be configured slidable on the tubing, at least before the tubing is coupled to the fluidic device. The receiving cavity may be configured for accommodating the back ferrule and a part of the first joining element. The fitting element may comprise an additional spring element arranged slidable on the tubing between the back ferrule and first joining element to transmit a force exerted by the first joint element to back ferrule.

Any of the sealing piece, the front ferrule, the back ferrule, spring elements, and the joint element may be embodied as disclosed by the documents cited in the introductory part of the description and in particular in the aforementioned WO 2010/000324 A1, which teaching with respect to the front ferrule shall be incorporated herein by reference.

The term "fluidic device" as used herein may cover or refer to a tubing or an apparatus such as an HPLC device, a fluid separation device, a fluid handling device, and/or a measurement device in general. Accordingly, embodiments of the invention cover couplings between individual tubings as well as couplings between a tubing and a device/apparatus.

The fluidic device may comprise a processing element configured for interacting with a sample fluid. The fluidic device may be configured to conduct a sample fluid through the fluidic device, a fluid separation system for separating compounds of a sample fluid, a fluid purification system for purifying a sample fluid, and/or to analyze at least one physical, chemical and/or biological parameter of at least one compound of a sample fluid.

An embodiment of the present invention comprises a fitting configured for coupling a tubing to a fluidic device. The fitting comprises a fitting element having the tubing, a first sealing element, and a second sealing element. The fluidic device comprises a receiving cavity configured for receiving the fitting element. Upon coupling of the tubing to the fluidic device, the first sealing element provides a first sealing stage at a front side of the tubing where the tubing is pressing to a contact surface within the receiving cavity. The second sealing element provides a second sealing stage for sealing the receiving cavity along a side of the tubing within the receiving cavity. Such fitting provides a two-stage sealing as aforediscussed, and may thus provide a chromatographic sealing by the first sealing element at the front side of the tubing and a system sealing by the second sealing stage. The second sealing stage thus seals an interspace between the first and second sealing stages.

An embodiment of the present invention comprises a fluid separation system configured for separating compounds of a sample fluid in a mobile phase. The fluid separation system comprises a mobile phase drive, such as a pumping system, configured to drive the mobile phase through the fluid separation system. A separation unit, which can be a chromatographic column, is provided for separating compounds of the sample fluid in the mobile phase. The fluid separation system further comprises a fitting element and/or fitting as disclosed in any of the aforementioned embodiments for coupling a tubing (provided the conducting the mobile phase) to a fluidic device in such fluid separation system. The fluid separation system may further comprise a sample injector configured to introduce the sample fluid into the mobile phase, a detector configured to detect separated compounds of the sample fluid, a collector configured to collect separated compounds of the sample fluid, a data processing unit configured to process data received from the fluid separation system, and/or a degassing apparatus for degassing the mobile phase. The fluidic device to which the tubing is or can be coupled can be any of such devices, and plural of such fittings or fitting elements may be used within such fluid separation system.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see the website agilent.com).

One embodiment comprises a pumping apparatus having a piston for reciprocation in a pump working chamber to compress liquid in the pump working chamber to a high pressure at which compressibility of the liquid becomes noticeable.

One embodiment comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (e.g. from the supply), thus allowing to provide a continuous flow at the output. However, it is clear that also both pumping apparatuses might be operated in parallel (i.e. concurrently), at least during certain transitional phases e.g. to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift.

The separating device preferably comprises a chromatographic column providing the stationary phase. The column might be a glass or steel tube (e.g. with a diameter from 50 µm to 5 mm and a length of 1 cm to 1 m) or a microfluidic column (as disclosed e.g. in EP 1577012 A1 or the Agilent 1200 Series HPLC-Chip/MS System provided by the applicant Agilent Technologies, see, e.g., the website chem.agilent.com/Scripts/PDS.asp?lPage=38308). For example, a slurry can be prepared with a powder of the stationary phase and then poured and pressed into the column. The individual components are retained by the stationary phase differently and separate from each other while they are propagating at different speeds through the column with the eluent. At the end of the column they elute one at a time. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are micro-porous for an increased surface, though in EBA a fluidized bed is used.

The mobile phase (or eluent) can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic are delivered in separate bottles, from which the gradient pump delivers a programmed blend to the system. Other commonly used solvents may be isopropanol, tetrahydrofuran (THFU), hexane, ethanol, and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particularly 50-120 MPa (500 to 1200 bar).

The HPLC system might further comprise a sampling unit for introducing the sample fluid into the mobile phase stream, a detector for detecting separated compounds of the sample fluid, a fractionating unit for outputting separated compounds of the sample fluid, or any combination thereof. Further details of HPLC system are disclosed with respect to the aforementioned Agilent HPLC series, provided by the applicant Agilent Technologies, under the website agilent-.com which shall be incorporated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanying drawing(s). Features that are substantially or functionally equal or similar will be referred to by the same reference sign(s). The illustration in the drawing is schematic.

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

Figure 1:
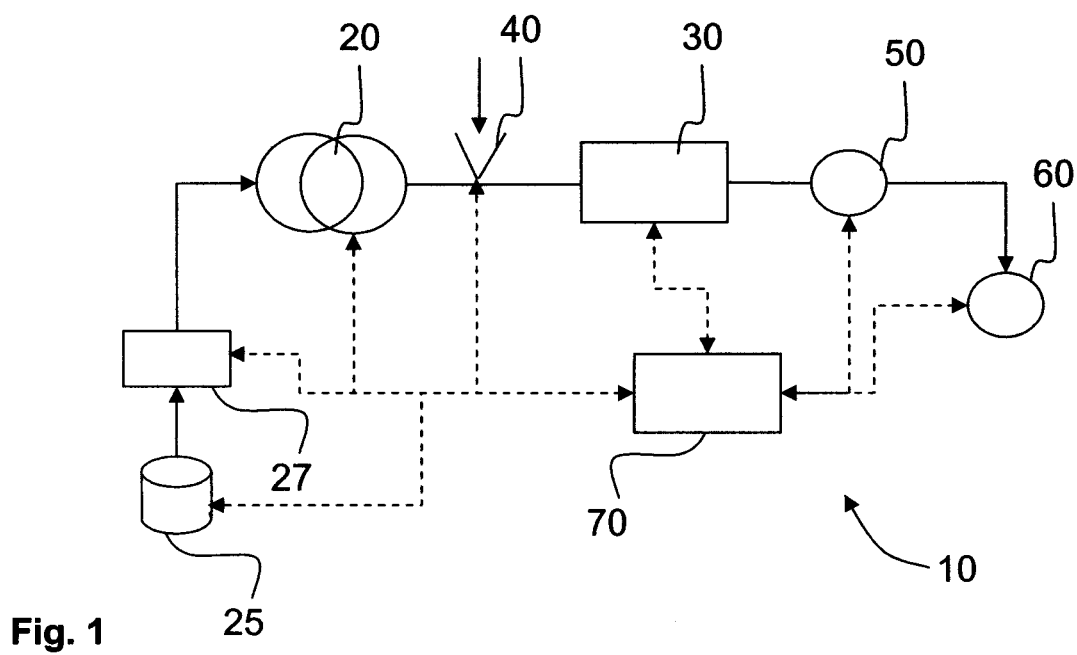
FIG. 1 shows in schematic view a liquid separation system 10, in accordance with embodiments of the present invention, e.g. used in high performance liquid chromatography (HPLC).

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

For transporting liquid within the liquid separation system 10, typically tubings (e.g. tubular capillaries) are used as conduits for conducting the liquid. Fittings are commonly used to couple plural tubings with each other or for coupling a tubing to any device. For example, fittings can be used to connect respective tubings to an inlet and an outlet of the chromatographic column 30 in a liquid-sealed fashion. Any of the components in the fluid path (solid line) in FIG. 1 may be connected by tubings using fittings. While the fluid path after the column 30 is usually at low pressure, e.g. 50 bar or below, the fluid path from the pump 20 to the inlet of the column 30 is under high pressure, currently up to 1200 bar, thus posing high requirements to fluid tight connections.

Figure 2:
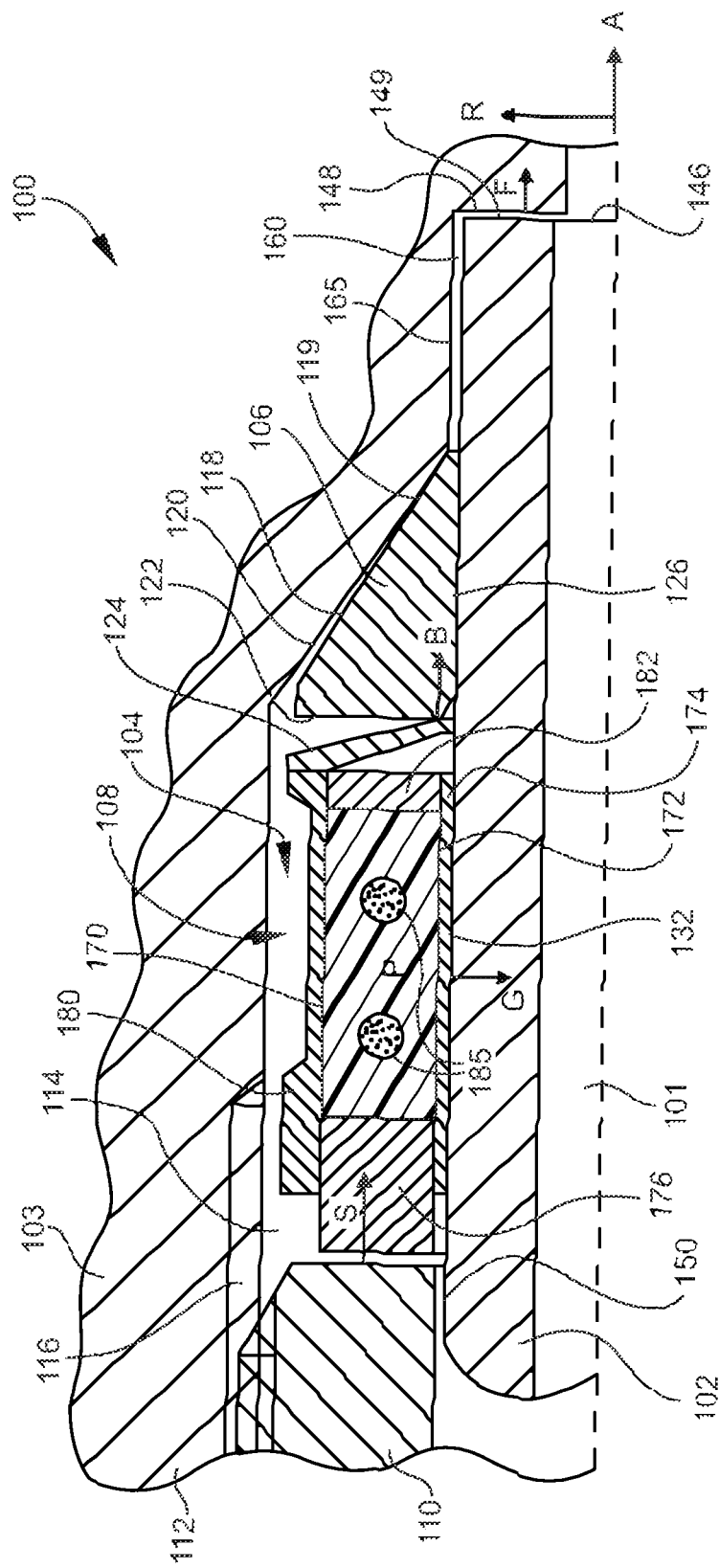
FIGS. 2 and 3 illustrate in cross-sectional view embodiments of a fitting 100.

FIG. 2 shows—in a cross-sectional part view—an embodiment of a high pressure fitting 100 for coupling a tubing 102 having an inner fluid channel 101 for conducting liquid, e.g. the mobile phase with or without a sample fluid) to another fluidic device 103, such as chromatographic column 30 of FIG. 1. In the schematic view of FIG. 2, only the portion of the device 103 which is relevant for the coupling with the tubing 102 is depicted.

The fitting 100 comprises a male piece 104 having a front ferrule 106 (e.g. made of a polymer material) and having a gripping piece 108, which will explained later in more detail. In the embodiment of FIG. 2, the front ferrule 106 and the gripping piece 108 are separate elements but may also be integrally formed as one element. Each of the front ferrule 106 and the gripping piece 108 is slidable over the tubing 102 (which might have a metal outer tubing or socket as known in the art). The male piece 104 further has a first joint element 110, which is also configured slidably on the tubing 102. For mounting the fitting 100 on the tubing 102, first the front ferrule 106 and the gripping piece 108, and then subsequently the first joint element 110 are slid on the tubing 102. The front ferrule 106, the gripping piece 108, and the first joint element 110 together constitute the male piece 104.

After having slid the male piece 104 over the tubing 102, a female piece 112 having a receiving cavity 114 (e.g. a recess) may be slid over the tubing 102 (from the right-hand side to the left-hand side of FIG. 2) or the male piece 104 may be inserted into the receiving cavity 114 of the female piece 112, dependent on the specific application and/or the specifics or type of the respective fluidic device 103. The receiving cavity 114 is configured for accommodating the front ferrule 106, the gripping piece 108, a part of the first joint element 110, and a part of the tubing 102. The receiving cavity 114 has a second joint element 116 configured to be joinable to the first joint element 110. The first and the second joint elements 110, 116 may be fastened to one another by a screw connection, as will be explained below in more detail.

A lumen 126 of the front ferrule 106 is dimensioned for accommodating the tubing 102 with clearance. A lumen 132 of the gripping piece 108 is dimensioned for accommodating the tubing 102 with clearance. The first joint element 110 also has a lumen 150 configured for accommodating the tubing 102 with clearance.

The gripping piece 108 is configured such that upon joining the first joint element 110 to the second joint element 116, the gripping piece 108 exerts in axial direction (as indicated by axis A) a pressing force B on the front ferrule 106 to provide a sealing between the front ferrule 106 and the female piece 112. Simultaneously, upon joining the gripping piece 108 exerts in radial direction (as indicated by axis R) a grip force G between the male piece 104 and the tubing 102. In addition to the gripping force G on the tubing 102, the gripping piece 108 exerts a front force F on the tubing 102 in axial direction A, which presses the tubing 102 against a contact surface of the receiving cavity 114 to provide a front-sided sealing of the tubing 102. The pressing force B as well as the front force F are in axial direction A (or parallel thereto), parallel to an extension of the tubing 102, whereas the grip force G is in radial direction R which is perpendicular to the extension of the tubing 102. With the grip force G, the gripping piece 108 provides a positive locking force between the male piece 104 and the tubing 102 and prevents the tubing 102 from laterally sliding after having fixed the two joint elements 110, 116 to one another.

As can be taken from FIG. 2, the front ferrule 106 has a conically tapered front part 118 shaped and dimensioned to correspond to a conical portion 120 of the receiving cavity 114 of the female piece 112. Thus, a form closure between the conical portion 120 of the receiving cavity 114, on the one hand, and the conically tapered front part 118 of the front ferrule 106 may be achieved. The front ferrule 106 has a back part 122, which may be conically tapered and also arranged vertically or upright, and may be shaped and dimensioned to correspond to a slanted annular front spring 124 of the gripping piece 108. Upon exertion of the pressing force P, the slanted annular front spring 124 may be bent and will thus provide the pressing force B to be elastic and spring-biased. Upon joining the first joint element 110 to the second joint element 116, the slanted annular front spring 124 is bent and promotes a forward motion of the front ferrule 106 towards a stopper portion 119 of the receiving cavity 114 of the female piece 112.

As will be explained later, the gripping piece 108 is configured to promote, upon joining the first joint element 110 to the second joint element 116, a forward motion of the tubing 102 towards a stopper portion 148 of the receiving cavity 114 of the female piece 112 providing a spring-loading force. The stopper portion 148 typically is provided by a contact surface of the receiving cavity 114 to which a front side 149 of the tubing 102 is abutting to.

The first joint element 110 is configured for being joined to the second joint element 116 by a screw connection. An external thread in the first joint element 110 of the male piece 104 can be screwed into an internal thread of the female piece 112. By fastening such screwing connection, the first joint element 110 exerts a force S on the gripping piece 104, which leads to (1) gripping between the gripping piece 104 and the tubing 102 under the influence of the gripping force G, (2) a front-sided sealing between the front side 149 of the tubing 102 and the receiving cavity 114 under the influence of the front force F, and (3) a side sealing between the front ferrule 106 and the receiving cavity 114 under the influence of the pressing force P transmitted by the pressing force B.

FIG. 2 shows a non-biased state of the fitting 100. In a sealed configuration, the side sealing is achieved between the front ferrule 106 and the female part 112, and the front sealing is achieved in between the front side 149 and the female part 112. The front side 149 of the tubing 102 may be provided with a (e.g. polymeric) coating in order to further reduce sample contamination by increasing the sealing performance between the front side 149 and the stopper portion 148.

In the following, the force transmission will be explained: After having slid the front ferrule 106 and the gripping piece 108 on the tubing 102 and after having slid the first joint element 110 onto the tubing 102, the first joint element 110 may be connected by screwing with the second joint element 116. This converts the gripping piece 108 into a biased state, so that grip is generated between the tubing 102 and the gripping piece 108. As the grip force increases, the axial forces B and F longitudinal to the capillary axis increase analog and provide the front and side sealing.

Turning now in greater detail to the gripping piece 108, as already illustrated, the gripping piece 108 is configured to exert—upon coupling of the tubing 102 to the fluidic device 103—the grip force G between the male piece 104 of the fitting 100 and the tubing 102. For that purpose, the gripping piece 108 comprises a hydraulic element 170, which is configured to transform the axial force S into a hydraulic pressure P within the hydraulic element 170. The hydraulic pressure P then in turn causes the grip force G.

In the embodiment of FIG. 2, the hydraulic element 170 is a fluid, such as a liquid, an oil, or a grease. Alternatively, a gel or a plastic material, such as polymer, can be used as well, for example polyurethane or polytetrafluoroethylene (PTFE, e.g., TEFLON® material). The hydraulic element 170 transforms the applied force S into the isotropic pressure P, which applies independently of the direction of applied force S. Accordingly, the grip force G results from the hydraulic pressure P applied on a contact surface 172 of the hydraulic element 170 towards the tubing 102. In case the hydraulic element 170 is retained in a housing, which may be provided as an integral part or result from plural sides abutting together as in the embodiment of FIG. 2, the contact surface 172 is provided by the hydraulic element 170 abutting to a lower surface 174 of such housing, which further abuts to the front side 182 of the gripping piece 108. The parts comprising the contact surface 172, the lower surface 174, and the front side 182 are fixed to each other.

The gripping piece 108 in FIG. 2 further comprises a piston 176, which can be moved under the influence of the applied axial force S into the direction of such force S as depicted in FIG. 2. The first joint element 110, upon being joined to the second joint element 112, pushes the piston 176. This in turn increases the hydraulic pressure P, so that with (e.g.) screwing the first joint element 110 to the second joint element 112 the hydraulic pressure P (continuously) increases. With increasing the hydraulic pressure P, the grip force G also increases, thus leading to securely gripping the gripping piece 108 to the tubing 102. As apparent from FIG. 2, the gripping force G not only increases with increasing pressure P but also when the effective contact area 172 of the hydraulic element 170 towards the tubing 102 increases, or the area of the piston 176 decreases.

As the hydraulic pressure P applies substantially homogeneously onto the active contact surface 172, the profile of the grip force along the active contact surface 172 will be substantially flat. In other words, the hydraulic element 170 provides a substantially constant grip force G over the entire active contact surface 172 where the hydraulic element 170 is facing towards the tubing 102. This allows dimensioning and guiding the grip force by adequately designing the active contact surface 172. For example, by increasing the active contact surface 172 while maintaining the hydraulic pressure at the same level, the grip force can be increased substantially in proportion to the increase of the contact surface 172.

The hydraulic element 170 is enclosed at its upper side by a spring bushing 180. In the embodiment of FIG. 2, the spring bushing 180 is designed to be elastically deformable, for example by providing a portion having a smaller thickness as depicted in FIG. 2. Accordingly, the spring bushing 180 will be elastically deformed under the influence of the hydraulic pressure P, which in turn causes the grip force G to be spring biased. This allows compensating, for example, for settling down, creeping or leakage of the hydraulic material.

Alternatively or in addition to the elastic deformability of the spring bushing 180, the hydraulic element 170 might comprise gas inclusions 185, as exemplarily depicted in FIG. 2. Such gas inclusions 185 will collapse under the influence of the hydraulic pressure P but provide an elastic counterforce against the volume decrease.

In the embodiment of FIG. 2, the front spring 124 is provided as individual component, but may also be an integral part of the spring bushing 180. As explained above, the front spring 124 also causes the pressing force B to be spring loaded in order to elastically seal the front ferrule 106 to the side 120. The front spring 124 may be omitted in case either the pressing force B does not have to be spring-biased or the hydraulic element 170 is configured to be at least partly elastic (for example due to the gas inclusions 185 or the elastically deformed spring bushing 180) and provides an elastically deformation on the front side 182 of the gripping piece 108. In the latter case, a front side 182 of the gripping piece 108 can abut directly to the front ferrule 106. Alternatively, the front ferrule 106 can be provided as an integral part of the gripping piece 108 and the back part 122 of the front ferrule 106 may directly be in contact with the hydraulic element 170.

Figure 3:
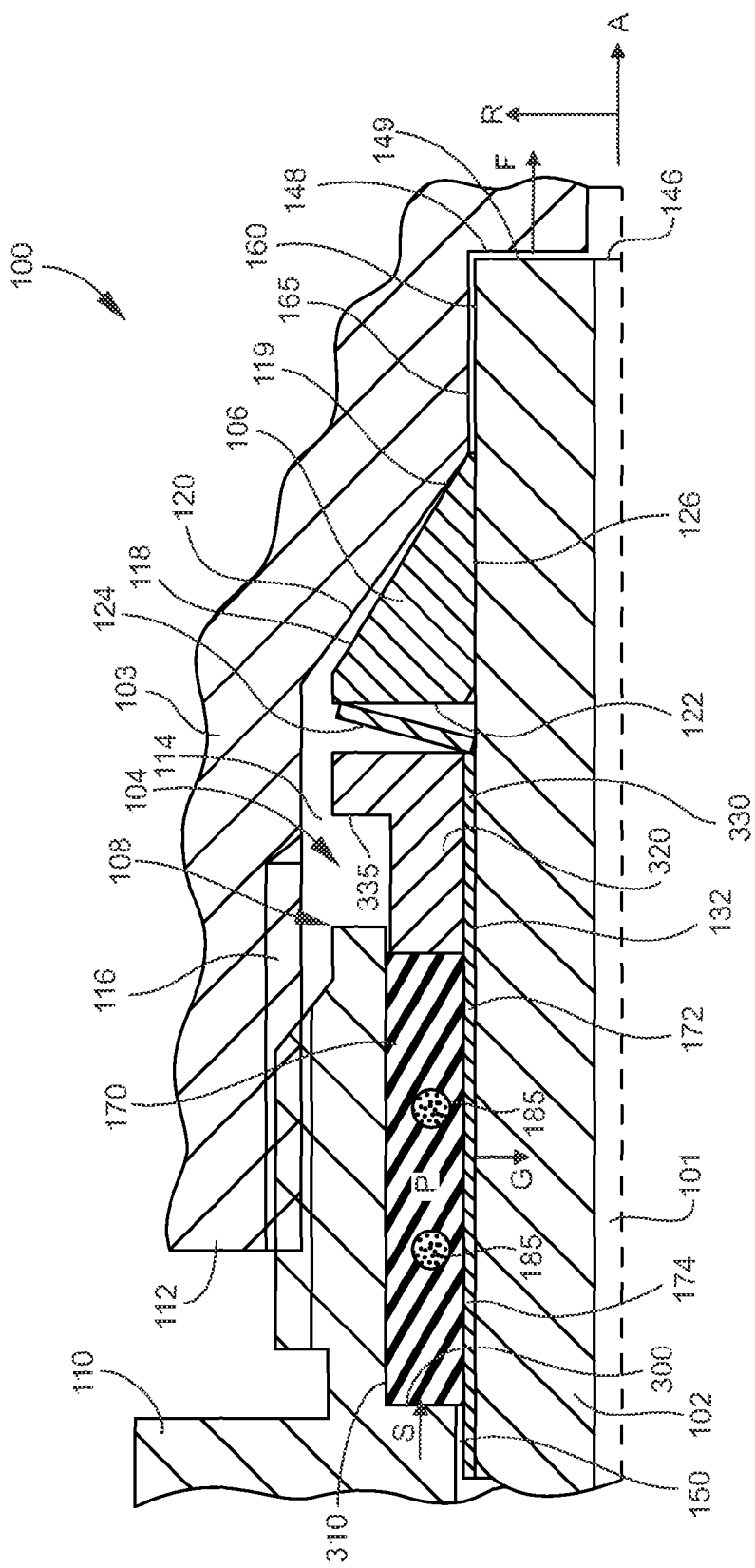

FIG. 3 shows an alternative embodiment of the fitting 100. Only the features differing from FIG. 2 shall be explained the following. In the embodiment of FIG. 3, the fitting screw of the first joint element 110 now encloses and houses the hydraulic element 170 at a front side 300 and a top side 310. A front part 320 is fixedly coupled to a lower side 330 of the gripping piece 108. Accordingly, the first joint element 110 (with its sides 300 and 310) together with the front element 320 and the lower side 330 enclose and house the hydraulic element 170. In the embodiment of FIG. 3, the first joint element 110 incorporates the spring bushing 180. This may allow extending the size of the gripping piece 108 backwards along the first joint element 110 or reduce the overall length of the male piece 104 and/or reduce the required elements involved.

The front element 320 may provide a stopper 335 to margin the compression of the hydraulic element 170.

The front part 320 and the front ferrule 106 may be the same part e.g. a molded piece which incorporates the gripping piece 108. Further, the front spring 124 could be integrated as a separated part or as part of the gripping piece 108.

While the front sealing at the front side 149 may be sufficient in certain applications, it may not be sufficient in particular for high pressure applications, for example when applying fluid pressure within the flow path of the tubing 102, e.g. in the range of 100-1500 bar, dependent on the materials used in the components connecting at the front side of the fitting 100. The side sealing by the front ferrule 106 provides the required high pressure sealing. The gripping piece 108 presses, upon coupling of the tubing 102 to the fluidic device 103—against the region 148. This closes and seals an interspace 160 around the front portion of the tubing 102 extending from the front side 149 over a lateral side 165 up to the region where the front ferrule 106 seals against the side 120. Having a two-stage sealing also provides an additional design parameter in balancing the requirements of (1) adapting to the geometry of the contacting areas and (2) a degree of deformation in particular of the flow path (as a result of applying a high contact pressure). For example, the first stage of sealing provided by the front sealing at the front side 149 might be purposely designed to seal against a lower pressure only for the benefit of limiting deformation and thus constriction in the flow path.

During pressurization of the flow path 101 in the tubing 102, when increasing fluid pressure to a target system pressure, liquid might leak through the primary front sealing stage provided at the front side 146 into the interspace 160. By designing the (secondary) side sealing stage provided by the front ferrule 106 to fully seal against the maximum pressure within the flow path 101, liquid may fill the interspace 160 until the pressure difference between the system pressure and the pressure within the interspace 160 reaches the sealing pressure capability of the (primary) front sealing. Since the front sealing can be optimized to the capability for the optimal pressure difference, the side sealing can be optimized to the system pressure required. The split in two functional or cascaded pressures drops as achieved by a primary and a secondary sealing e.g. allows the primary sealing design to be kept unmodified while the system pressure requirements can be solved within the secondary sealing.

The invention claimed is:

1. A fitting element, in particular for an HPLC application, configured for providing a fluidic coupling of a tubing to a fluidic device, the fitting element comprising:
    a gripping piece configured to exert, upon coupling of the tubing to the fluidic device, a grip force (G) between the fitting element and the tubing, wherein the gripping piece comprises a hydraulic element configured to transform an axial force (S) into a hydraulic pressure (P) within the hydraulic element;
    a housing for housing the hydraulic element and for retaining the hydraulic element in a certain space, wherein the gripping piece at least partially defines the housing;

a rigid piston movable in an axial direction of an elongation of the tubing for contacting the hydraulic element and exerting the axial force (S) on the hydraulic element; and a first joint element movable in the axial direction for contacting the piston and pushing the piston in the axial direction and into contact with the hydraulic element, wherein:

the first joint element is configured for movably engaging a second joint element of the fluidic device by a screw connection, such that movably engaging the second joint element moves the first joint element in the axial direction; and the hydraulic pressure (P) in the hydraulic element causes the grip force (G).

2. The fitting element of claim 1, wherein the hydraulic element is an isotropic hydraulic element, comprising at least one of:

the isotropic hydraulic element is configured to transform an applied force into an isotropic pressure within the hydraulic element;

the isotropic hydraulic element is configured to transform an applied force into an isotropic pressure within the hydraulic element, at least after a given time period or at a given time constant;

the isotropic hydraulic element is configured so that pressure at a boundary surface of the hydraulic element is substantially equal over the boundary surface;

the isotropic hydraulic element is configured to exert substantially the same force on each respective standardized surface element of a boundary surface.

3. The fitting element of claim 1, wherein the hydraulic element is an anisotropic hydraulic element, comprising at least one of:

the anisotropic hydraulic element is configured to transform an applied force into a pressure distribution within the hydraulic element;

the anisotropic hydraulic element is configured to transform an applied force into a pressure distribution within the hydraulic element at least after a given time period or at a given time constant;

the anisotropic hydraulic element is configured so that pressure at a boundary surface of the hydraulic element varies in accordance with a pressure distribution;

the anisotropic hydraulic element is configured so that a force exerted on a respective standardized surface element at a boundary surface varies in accordance with a pressure distribution.

4. The fitting element of claim 1, wherein the hydraulic element is selected from the group consisting of: a fluid, a liquid, an oil, a pressure oil, grease, a gel, polysiloxane, a silicone gel, a solid material having elasticity, an elastomer, a plastic material, a polymer having plasticity, rubber, polyurethane, and polytetrafluoroethylene.

5. The fitting element of claim 1, wherein the hydraulic element has a configuration selected from the group consisting of:

the hydraulic element has a viscosity in a range of 250 to 100,000 mPa*s;

the hydraulic element has a viscosity in a range of 1000 to 25,000 mPa*s;

the hydraulic element has a hardness in a range of 10 to 100 Shore A and 30 to 100 Shore D;

the hydraulic element has a hardness in a range of 70 Shore A to 80 Shore D;

the hydraulic element comprises a polyurethane elastomer;

the hydraulic element comprises a polyurethane elastomer having a hardness of about 90 Shore A;

the hydraulic element has an elasticity measured in elongation before break in a range of 10 to 1000%; and the hydraulic element has an elasticity measured in elongation before break in a range between 30% and 100%.

6. The fitting element of claim 1, wherein:

the hydraulic element has an active contact surface directed towards the tubing, the active contact surface transforms the hydraulic pressure (P) into the grip force (G), and the size of the contact surface is configured to adjust to at least one of a desired magnitude and a desired profile of the grip force (G).

7. The fitting element of claim 6, comprising at least one of:

the hydraulic element has a surface abutting to the tubing, and the plane surface substantially represents the active contact surface;

the hydraulic element has one of a plane surface, a cylindrical surface, or a surface slotted along the direction of the axis;

the active contact surface exerts a substantially homogeneous profile of the grip force (G) along the axial direction.

8. The fitting element of claim 1, wherein:

the gripping piece is configured for generating, upon coupling of the tubing to the fluidic device, a spring-biased force.

9. The fitting element claim 8, comprising at least one of:

the spring-biased force is exerted in an axial direction being a direction of an axial elongation of the tubing or parallel thereto;

the spring-biased force is exerted in a radial direction being a direction perpendicular to an axial elongation of the tubing or parallel thereto.

10. The fitting element of claim 8, comprising at least one of:

the gripping piece is configured for exerting the spring-biased force in a radial direction on the tubing in order to provide a spring-biased grip force (G) onto the tubing;

the gripping piece is configured for exerting the spring-biased force in an axial direction on the tubing in order to provide a spring-biased coupling of the tubing to the fluidic device;

the gripping piece is configured for exerting the spring-biased force in an axial direction on a sealing piece in order to provide a spring-biased sealing between the sealing piece and the fluidic device.

11. The fitting element of claim 8, wherein the spring-biased force is generated by at least one of:

a mechanical spring element, a spring washer, a disk spring, or a Belleville spring washer;

a multiple spring configuration, or a spring configuration comprising two disk springs in parallel or mirrored;

an elastic shaping configured to generate the spring-biased force, or a collar elastically expanding its diameter.

12. The fitting element of claim 8, wherein the spring-biased force is generated by the hydraulic element, and the hydraulic element comprises, for exerting the spring-biased force, at least one of:

one or more gas inclusions;

a material having a compressibility at the working pressure in a range of 5 to 30%;

an at least partly elastic housing;

an elastic shaping configured to generate the spring-biased force.

13. The fitting element of claim 1, comprising at least one of:
a sealing piece configured to provide, upon coupling of the tubing to the fluidic device a sealing between the sealing piece and the fluidic device;
a front sealing configured to provide, upon coupling of the tubing to the fluidic device a sealing between a front side of the tubing coupling to the fluidic device and the fluidic device.

14. A fitting configured for coupling a tubing to a fluidic device, the fitting comprising:
a fitting element according to claim 1, configured for providing a fluidic coupling of the tubing to the fluidic device, and
wherein a receiving cavity of the fluidic device is configured for receiving the fitting element, and upon coupling of the tubing to the fluidic device the tubing is pressing to the receiving cavity and the fluid path of the tubing is connected to the fluid path of the fluidic device.

15. A fluid separation system for separating compounds of a sample fluid in a mobile phase, the fluid separation system comprising:
a mobile phase drive, preferably a pumping system, configured to drive the mobile phase through the fluid separation system,
a separation unit, preferably a chromatographic column, configured for separating compounds of the sample fluid in the mobile phase,
and a fitting element according to claim 1 for coupling a tubing for conducting the mobile phase.

16. A fitting element, in particular for an HPLC application, configured for providing a fluidic coupling of a tubing to a fluidic device, the fitting element comprising:
a gripping piece configured to exert, upon coupling of the tubing to the fluidic device, a grip force (G) between the fitting element and the tubing, wherein the gripping piece comprises a hydraulic element configured to transform an axial force (S) into a hydraulic pressure (P) within the hydraulic element;
a housing for housing the hydraulic element and for retaining the hydraulic element in a certain space, wherein the gripping piece at least partially defines the housing along a lower side of the hydraulic element;
a first joint element configured to move in an axial direction of an elongation of the tubing, the first joint element having a front side in contact with a back surface of the hydraulic element to exert the axial force (S) on the hydraulic element, and a top side extending from the front side over a top surface of the hydraulic element, wherein the first joint element partially defines the housing of the hydraulic element along the back surface and the top surface of the hydraulic element; and a front element fixedly coupled to the lower side of the gripping piece to contact a front surface of the hydraulic element defining a front part of the housing;
wherein the hydraulic pressure (P) in the hydraulic element causes the grip force (G).

17. The fitting element of claim 16, wherein the hydraulic element is an isotropic hydraulic element, comprising at least one of:
the isotropic hydraulic element is configured to transform an applied force into an isotropic pressure within the hydraulic element;
the isotropic hydraulic element is configured to transform an applied force into an isotropic pressure within the hydraulic element, at least after a given time period or at a given time constant;
the isotropic hydraulic element is configured so that pressure at a boundary surface of the hydraulic element is substantially equal over the boundary surface;
the isotropic hydraulic element is configured to exert substantially the same force on each respective standardized surface element of a boundary surface.

18. The fitting element of claim 16, wherein the hydraulic element is selected from the group consisting of: a fluid, a liquid, an oil, a pressure oil, grease, a gel, polysiloxane, a silicone gel, a solid material having elasticity, an elastomer, a plastic material, a polymer having plasticity, rubber, polyurethane, and polytetrafluoroethylene.

19. The fitting element of claim 16, wherein the hydraulic element has a configuration selected from the group consisting of:
the hydraulic element has a viscosity in a range of 250 to 100,000 mPa*s;
the hydraulic element has a viscosity in a range of 1000 to 25,000 mPa*s;
the hydraulic element has a hardness in a range of 10 to 100 Shore A and 30 to 100 Shore D;
the hydraulic element has a hardness in a range of 70 Shore A to 80 Shore D;
the hydraulic element comprises a polyurethane elastomer;
the hydraulic element comprises a polyurethane elastomer having a hardness of about 90 Shore A;
the hydraulic element has an elasticity measured in elongation before break in a range of 10 to 1000%; and
the hydraulic element has an elasticity measured in elongation before break in a range between 30% and 100%.

20. The fitting element of claim 16, wherein:
the hydraulic element has an active contact surface directed towards the tubing, the active contact surface transforms the hydraulic pressure (P) into the grip force (G), and the size of the contact surface is configured to adjust to at least one of a desired magnitude and a desired profile of the grip force (G).

21. The fitting element of claim 16, wherein:
the front element includes a stopper extending radially away from the tubing to margin the compression of the hydraulic element.

* * * * *